(12) United States Patent
Park

(10) Patent No.: US 8,072,212 B2
(45) Date of Patent: Dec. 6, 2011

(54) MAGNETIC RESONANCE IMAGING METHOD AND APPARATUS WITH PHASE-SENSITIVE FLUID SUPPRESSION

(75) Inventor: Jaeseok Park, Seoul (KR)

(73) Assignee: Siemens Aktiengesellschaft, Munich (DE)

( * ) Notice: Subject to any disclaimer, the term of this patent is extended or adjusted under 35 U.S.C. 154(b) by 210 days.

(21) Appl. No.: 12/554,384

(22) Filed: Sep. 4, 2009

(65) Prior Publication Data

US 2010/0060278 A1 Mar. 11, 2010

(30) Foreign Application Priority Data

Sep. 5, 2008 (DE) .................. 10 2008 046 022

(51) Int. Cl.
*G01V 3/00* (2006.01)
(52) U.S. Cl. ...................... 324/309; 324/307
(58) Field of Classification Search .......... 324/300–322; 600/407–445
See application file for complete search history.

(56) References Cited

U.S. PATENT DOCUMENTS

| | | | |
|---|---|---|---|
| 4,893,081 A * | 1/1990 | Zur | 324/309 |
| 6,670,812 B1 * | 12/2003 | Mock et al. | 324/309 |
| 6,801,800 B2 * | 10/2004 | Miyazaki et al. | 600/410 |
| 7,164,268 B2 | 1/2007 | Mugler, III et al. | |
| 2007/0238973 A1 * | 10/2007 | Krueger | 600/410 |

OTHER PUBLICATIONS

"Magnetresonanztomographie," Nitz, Der Radiologe, vol. 43 (2005) pp. 745-765.
"Entwicklung, Optimierung and klinische Erprobung von $T_2$-Gewichteten Messverfahren mit Reduzierter Hochfrequenzleistung für die Kernspintomographie," Matthias Weigel Dissertation, Albert-Ludwigs-Universtät, Freiburgmim Breisgau, Germany (2007).
"Assessment of Cerebral Gliomas by a New Dark Fluid Sequence HIRE (High Intensity Reduction)," Essig et al, Proc. Intl. Soc. Mag. Reson. Med., vol. 8, (2000) p. 386.

* cited by examiner

*Primary Examiner* — Brij Shrivastav
(74) *Attorney, Agent, or Firm* — Schiff Hardin LLP

(57) ABSTRACT

In a method and magnetic resonance (MR) apparatus to separate a signal component of a cerebrospinal fluid from other signal components in the acquisition of MR images of an examination subject, a first signal acquisition with spin echo-based signals is executed, in which the signal components of the cerebrospinal fluid and the other signal components have the same phase position, and a second signal acquisition with spin echo-based signals is then executed, in which the signal components of the cerebrospinal fluid and the other signal components have an opposite phase position. An MR image with signals of the other signal components is determined based on the two signal acquisitions with the signal component of the cerebrospinal fluid is significantly suppressed.

12 Claims, 4 Drawing Sheets

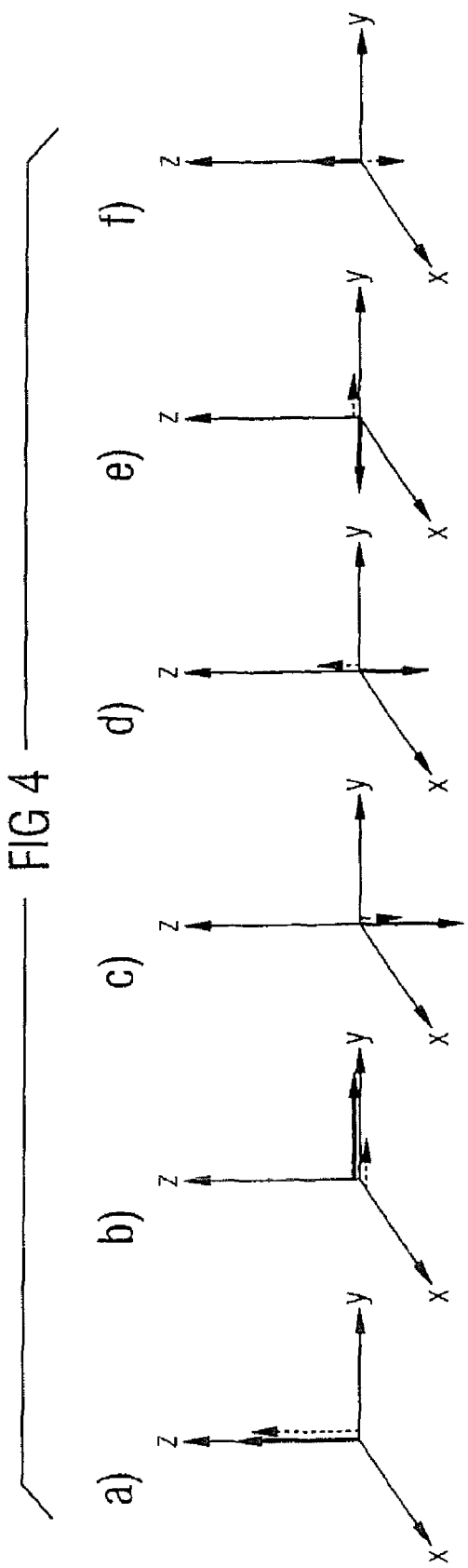

MAGNETIC RESONANCE IMAGING METHOD AND APPARATUS WITH PHASE-SENSITIVE FLUID SUPPRESSION

BACKGROUND OF THE INVENTION

1. Field of the Invention

The present invention concerns a method to separate a signal component of a cerebrospinal fluid from other signal components in the acquisition of MR images of an examination subject. The invention is particularly suitable for use in the acquisition of MR images of the brain.

2. Description of the Prior Art

Cerebrospinal fluid (CSF) is a clear, colorless liquid that fills the cerebral ventricles and the spinal canal and protects the brain and the spinal cord from shocks, and serves as a medium for material exchange. Cerebrospinal fluid has a long $T_2$ relaxation time which leads to a very bright signal in $T_2$ weighted images of the brain. Pathologies in the brain, for example multiple sclerosis (MS), likewise have a relatively long $T_2$ relaxation time, such that the strong signal of the cerebrospinal fluid can occlude the signals of the pathological tissue in $T_2$-weighted images of the brain. For this reason the signal portion of cerebrospinal fluid should be suppressed for a precise diagnosis.

In order to eliminate the CSF signal portions, it is known to use an IR (inversion recovery) preparation pulse in connection with a long inversion time TI due to the long $T_1$ relaxation time of the cerebrospinal fluid. However, this long IR preparation phase increases the total acquisition time of the images to a significant degree and leads to a reduced contrast between white and grey brain matter. For this reason the application of an IR preparation for $T_2$-weighted images with CSF suppression is not possible.

Furthermore, M. Essig et al. "Assessment of Cerebral Gliomas by a New Dark Fluid Sequence HIRE (High Intensity Reduction)" in Proc. Intl. Soc. Mag. Reson. Med. 8, 2000, Page 386 discloses acquiring two images with different contrast in a single measurement, wherein one image is $T_2$-weighted while the other image is very strongly $T_2$-weighted. Almost exclusively CSF signal contributions exist in the very strongly $T_2$-weighted image due to the long $T_2$ time. In this method, the second image is used as a scale for the cerebrospinal fluid, wherein a CSF-suppressed $T_2$-weighted image is generated by a subtraction of the two images. However, since pathologies as well as multiple sclerosis have a relatively long $T_2$ time, the pathological signals can likewise be reduced by the subtraction of the two images.

SUMMARY OF THE INVENTION

An object of the present invention is to provide a method in which the signal portions of the cerebrospinal fluid are separated from the signal portions of other tissue components in $T_2$-weighted exposures.

This object is achieved by a method to separate a signal component of a cerebrospinal fluid from other signal components in the acquisition of MR images of an examination subject, wherein according to the invention, a first signal acquisition is executed with spin echo-based signals, with the signal component of the cerebrospinal fluid and the other signal components having the same phase position in this first signal acquisition. Furthermore, a second signal acquisition with spin echo-based signals is executed in which the signal component of the cerebrospinal fluid and the other signal components have an opposite phase position. This means that, given the spin echoes in the first signal acquisition, the echoes of the two components have the same phase position while, in the second signal acquisition, the two signal components have the opposite phase position. An MR image with signals of the other signal components and with suppressed signal component of the cerebrospinal fluid can be subsequently determined based on the two signal acquisitions. With the method according to the invention it is possible to generate an MR image that essentially contains only the other signal components (such as signals of the grey and white brain matter), wherein the signal component of the cerebrospinal fluid is essentially suppressed, and thus pathological tissue structures cannot be occluded. With the two signal acquisitions it is possible to separate tissue components that do not differ due to a different resonance frequency (for instance fat and water) but rather have essentially the same resonance frequency, and to calculate an image in which the one tissue component is suppressed.

After the first signal acquisition and before the second signal acquisition, a wait occurs for a first time span $T_{Relax1}$ that is smaller than the $T_1$ time constant of the cerebrospinal fluid. If the two signal acquisitions are repeated with a repetition time TR, after the second signal acquisition and before the next first signal acquisition the method waits for a time span $T_{Relax2}$ that is longer than $T_{Relax1}$. The two time spans $T_{Relax1}$ and $T_{Relax2}$ can hereby be selected so that $T_{Relax2}$ is between 3 and 50 times longer than $T_{Relax1}$. For example, the time span $T_{Relax1}$ can be between 100 and 150 ms while the time span $T_{Relax2}$ can advantageously be between 500 and 5000 ms. The imaging sequence thus has the following workflow: first signal acquisition; $T_{Relax1}$; second signal acquisition; $T_{Relax2}$; followed by the next first signal acquisition. To separate the phase position of the cerebrospinal fluid and the phase position of the other components, the magnetization is advantageously inverted at the end of the first signal acquisition, meaning that it is aligned opposite to the direction of the polarization field Bo. The direction of the polarization field that is responsible for the polarization of the protons in the magnetic field is typically indicated with z, such that after the inversion the magnetization lies in the direction of the −z-axis.

Both the magnetization component of the cerebrospinal fluid and the other signal components are hereby inverted. Due to the different $T_1$ times of the cerebrospinal fluid and the other tissue components, via the time span $T_{Relax1}$ it can be achieved that the magnetization component of the cerebrospinal fluid is aligned opposite to the magnetization component of the other tissue components. This can in particular be achieved in that the first time span $T_{Relax1}$ is selected such that, after expiration of $T_{Relax1}$, the magnetization component of the cerebrospinal fluid is still aligned opposite to the direction of the polarization field while the magnetization component of the other signal components is already aligned parallel to the direction of the polarization field due to the shorter $T_1$ time. In the second signal acquisition, this opposite phase position is then retained upon radiation of the RF pulses such that resulting spin echoes have an opposite phase position.

For an optimization of the signal before inversion of the magnetization at the end of the first signal acquisition, a pulse series can be used for inversion, wherein RF pulses are radiated first that maximize the magnetization in the transversal plane perpendicular to the polarization field before this maximized magnetization is then inverted opposite to the direction of the polarization field. For example, two RF pulses with different flip angles can be used to maximize the transversal magnetization.

Furthermore, for signal optimization it is possible to use variable flip angles in the refocusing pulses to generate spin echo trains. As is typical in fast spin echo sequences, in an excitation pulse and multiple refocusing pulses the signal difference between grey brain matter and white brain matter can in particular be maximized by the variable flip angles.

An MR image that essentially possesses only a signal portion of the other signal components can be calculated with the aid of the two signal acquisitions and a scaling factor $c_{csf}$, wherein this factor represents the signal ratio of the magnetization of the cerebrospinal fluid to the total signal in the second signal acquisition. The signals of the first signal acquisition and the second signal acquisition are measured, and the scaling factor $c_{csf}$ can be determined with the aid of the Bloch equations so that an essentially CSF-free MR image can be calculated when the two signal intensities and the factor $c_{csf}$ are known. In order to reduce the influence of signal portions in the second signal acquisition relative to noise, a cerebrospinal fluid mask can be formed before the reconstruction in that only pixels that have an image signal above a predetermined threshold are taken into account.

The invention furthermore concerns an MR system which is in the position to calculate an MR image of the other signal components and suppressed cerebrospinal fluid as explained above.

BRIEF DESCRIPTION OF THE DRAWINGS

FIG. 4 shows the development of the magnetization in the imaging sequence from FIG. 2.

DESCRIPTION OF THE PREFERRED EMBODIMENTS

Figure 1:
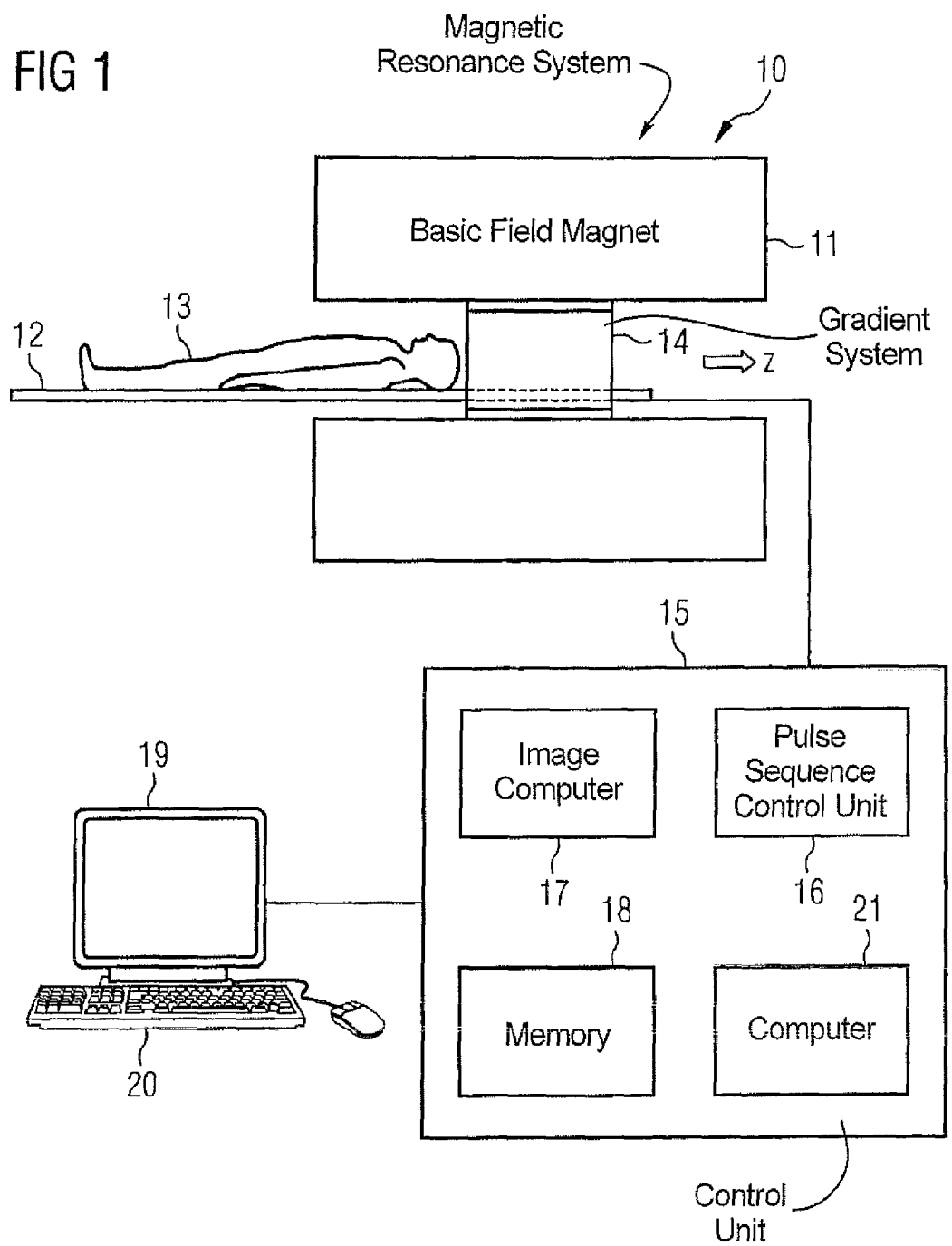
FIG. 1 schematically illustrates an MR system with which a method for separating cerebrospinal fluid from other signal components can be implemented.

In FIG. 1 a magnetic resonance (MR) system 10 is shown with whose help MR images can be generated in which the signal components of the cerebrospinal fluid can be suppressed to the greatest possible extent in $T_2$-weighted images of the brain. The MR system has a basic field magnet 11 to generate a polarization field $B_0$ that, for example, can run in the z-direction. To generate MR images, an examination subject 13 arranged on a bed 12 is driven into the basic field magnet 11 in order to there acquire exposures of the brain of the examination subject, for example. To generate the MR images, a gradient system 14 is provided to generate magnetic field gradients, an RF system (not shown) is provided to radiate RF pulses, and coils are provided to detect the signals induced by the RF radiation. In a control unit 15 which is used to control the workflow of the MR examination, a pulse sequence control unit 16, an image computer 17, a memory 18 and a display 19 with a control interface 20 are provided. The general functionality of an MR system to generate MR images via radiation of RF pulses and switching of gradients for localization of the detected signals is known to those skilled in the art need not be explained in detail herein. For clarity, only the elements that are of importance for the comprehension of the present invention are explained in detail.

The control unit 15 furthermore includes a computer 21 with which the MR image can be calculated, in which computer 21 the signal component of the cerebrospinal fluid is significantly suppressed while the other signal components in the MR image are present. How a generation of such an MR image is possible is described in detail in connection with FIGS. 2-4.

Figure 2:
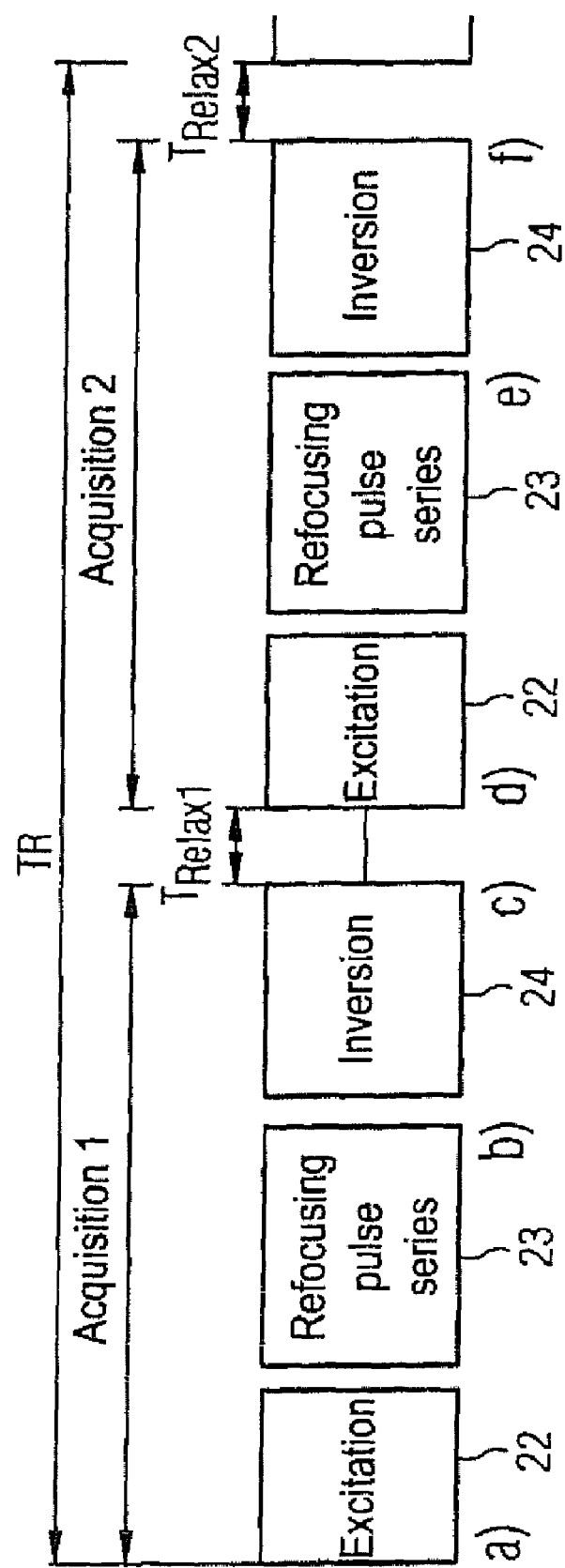
FIG. 2 is a sequence diagram to separate the two signal components.
Figure 3:
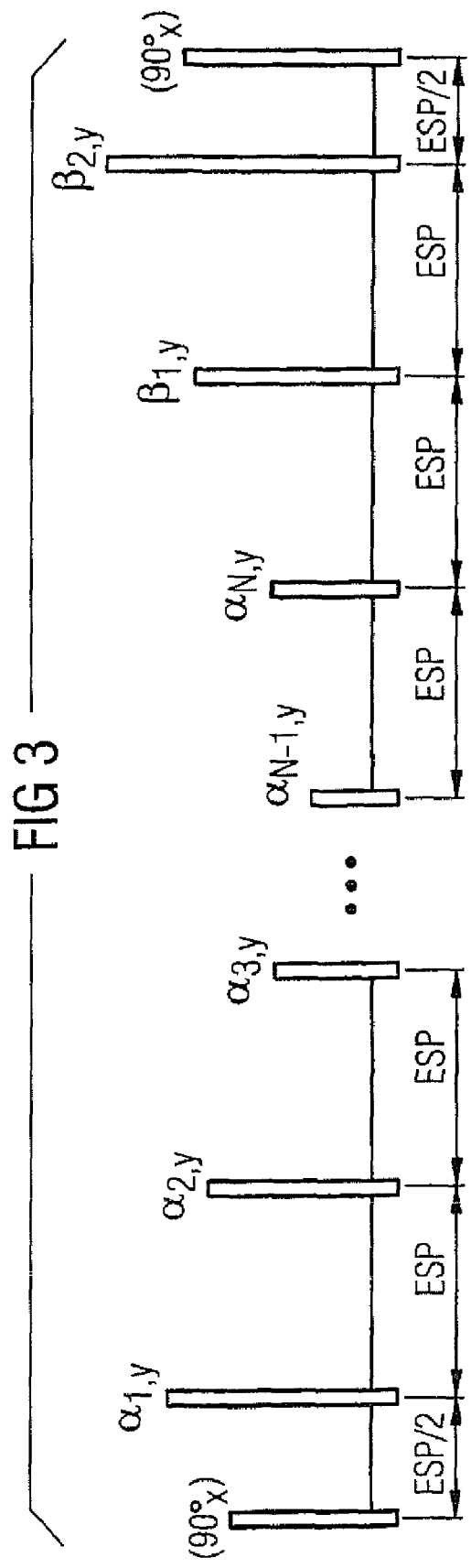
FIG. 3 shows the pulse series in the first and second signal acquisition.

Schematically presented in FIG. 2 is the pulse sequence with which MR images of the brain can be achieved with good signal contrast between white and grey brain matter, wherein the signal portion of the cerebrospinal fluid is minimized in $T_2$-weighted sequences. The imaging sequence used for imaging is a fast spin echo sequence with two acquisitions within one measurement. The pulse sequence scheme of the first acquisition possesses an excitation 22 that, for example, can be a non-selective excitation of the spins. After the excitation for the spin echo sequence (i.e. after the 90° pulse), the refocusing pulse 23 follows to generate the spin echoes, followed by an inversion or re-establishment pulse series 24 in which the remaining magnetization after the refocusing pulses is first maximized in the transversal plane before the magnetization is inverted in the directed opposite the direction of the polarization field $B_0$. The acquisition 2, which corresponds to the acquisition 1 with the same excitation 22, refocusing pulse series 23 and inversion 24, follows after a time span $T_{Relax1}$. Before the pulse sequence is repeated with the repetition time TR, a second time span $T_{Relax2}$ that is significantly larger than the time span $T_{Relax1}$ occurs after the end of the second acquisition. The pulse series of the two acquisitions 1 and 2 is described in detail in connection with FIG. 3. After the 90° excitation pulse (that, in the shown example, is a non-selective excitation pulse along the x-axis), the refocusing pulses $\alpha_{1,y}$ through $\alpha_{N,y}$ follow that are respectively spaced around the time span ESP. The interval between the 90° excitation pulse and the first refocusing pulse $\alpha_{1,y}$ is hereby ESP/2. As is apparent from the size of the bars that schematically represent the flip angle, at the beginning large flip angles are used (for example flip angles over)80°, wherein flip angles of 20°-25° are used after fewer than 5 RF pulses. The flip angle subsequently increases continuously, wherein at the conclusion the inversion pulse series with the RF pulses $\beta_{1,y}$, $\beta_{2,y}$ and the last inversion pulse is applied. The magnetization in the transversal plane reaches maximum with the two pulses $\beta_1$ and $\beta_2$ before this is inverted in the direction opposite to the polarization field with the last 90° pulse. The signal contrast between white and grey brain matter can be maximized via the pulse sequence shown in FIG. 3. The flip angles of the first two pulses of the inversion pulse series $\beta_1$ and $\beta_2$ can be calculated as follows:

$$\beta_{n,y} = \beta_{max}\cos(\lambda(2-n)), \quad n = 1, 2 \qquad (1)$$

$$\lambda = \frac{1}{2}\cos^{-1}\left(\frac{\alpha_{L,y}}{\beta_{max}}\right) \qquad (2)$$

wherein $\beta_{max}$, is the maximum angle that was selected with regard to the energy deposition in the body and the RF voltage. For example, $\beta_{max}$, can be 160°. $\alpha_{L,y}$ from Equation (2) is hereby the flip angle of the last RF pulse before the start of the inversion pulse series.

Within this long refocusing pulse train, the transversal magnetization of the cerebrospinal fluid relaxes very slowly due to the long $T_2$ relaxation time while the transversal magnetization of the remaining brain tissue relaxes relatively quickly, which leads to a greater signal of the cerebrospinal fluid relative to the other tissue components in the brain.

The magnetization of the cerebrospinal fluid and the magnetization of the remaining components are presented in the course of the pulse sequence in FIG. 4. The magnetizations shown in Images 4a-4f correspond to the points in time that correspond to the letters a-f in FIG. 2.

The solid arrow shows the magnetization of the cerebrospinal fluid while the dashed-line arrow represents the other tissue component (i.e. the non-cerebrospinal fluid). As is apparent in FIG. 4A, the magnetization of the cerebrospinal fluid an the magnetization of the remaining tissue components are aligned along the z-axis, parallel to the polarization field, before the beginning of the measurement. As is apparent in FIG. 4B, a magnetization is detected at the point in time b at the end of the refocusing pulse series. An echo for both signal components is generated along the y-axis due to the refocusing pulse series, wherein more magnetization of the cerebrospinal fluid than of the remaining tissue components is still present due to the longer $T_2$ time of the cerebrospinal fluid. The two magnetization components are aligned along the $-z$-direction at the point in time x due to the inversion pulse series. After the inversion, the two tissue components relax, meaning that the cerebrospinal fluid and the other tissue components revert into the starting position with the $T_1$ relaxation time constant. The time span $T_{Relax1}$ is now selected so that the magnetization of the cerebrospinal fluid still proceeds in a direction opposite to the z-axis before the next 90° excitation at the point in time d while a smaller magnetization portion of the remaining tissue again appears in the positive z-direction due to the shorter $T_1$ time. Due to the inversion and the subsequent first time span $T_{Relax1}$, the magnetization components of the cerebrospinal fluid and the other signal components could be separated from one another. Through the following second acquisition (which is identical to the first acquisition), an echo for the cerebrospinal fluid is respectively generated along the $-y$-axis after the 90° excitation pulse and the refocusing pulses while a smaller echo signal is generated along the positive y-axis for the other signal components, as is apparent from FIG. 4e. This means that echoes with opposite phase position are respectively generated in the second refocusing pulse series. Due to the subsequent 90° inversion pulse, the CSF magnetization is aligned again along the positive z-axis while the remaining magnetization is aligned along the negative $-z$-axis. By inserting the time span $T_{Relax2}$ with a time span between 500 and 5000 ms, the entire magnetization can again relax back into the positive z-axis. The calculation of the image that essentially possesses only signal portions of the other signal components and no signal portion of the cerebrospinal fluid is subsequently explained. Under consideration of the opposite phase development in acquisition 1 and 2, the signal intensities in the first acquisition $I_1$ and the signal intensity $I_2$ of the signal acquisition can be suppressed as follows $$I_1 = I_{csf} + I_{non-csf} \qquad (3)$$

$$I_2 = -c_{csf} I_{csf} + c_{non-csf} I_{non-csf} \qquad (4)$$

$$I_{non-csf} = \frac{c_{csf} I_1 + I_2}{c_{csf} + c_{non-csf}} \qquad (5)$$

wherein $I_{csf}$ is the signal intensity of the cerebrospinal fluid, $I_{non-csf}$ is the signal intensity of the other signal components and $c_{csf}$ and $c_{non-csf}$ are the scaling factors with which the signal intensities are respectively reduced in the second acquisition in comparison to the first acquisition. Since (as is apparent in FIG. 4d) $c_{non-csf}$ is much smaller than $c_{csf}$ due to the shorter relaxation time, Equation (5) can be written as follows $$I_{non-csf} = \frac{c_{csf} I_1 + I_2}{c_{csf} + c_{non-csf}} \approx \frac{c_{csf} I_1 + I_2}{c_{csf}} \qquad (6)$$

The scaling factor $c_{csf}$ can now be solved with the measurement parameters with the aid of the Bloch equation $$c_{csf} = \frac{1 + (M_{z,1,f} - 1)e^{-T_{relax1}/T_1}}{1 + (M_{z,2,f} - 1)e^{-T_{relax2}/T_2}} \qquad (7)$$

wherein $M_{z,1,f}$ is the longitudinal magnetization of CSF at the end of the first acquisition and $M_{z,2,f}$ is the longitudinal magnetization of CSF at the end of the second acquisition.

However, since the signal $I_2$ has a high CSF signal portion and a very low non-CSF signal portion, Equation (6) yields a very noisy image of the brain tissue since, due to the shorter $T_2$ time, the other signal components have only a very low signal portion. In order to prevent the noise of the image from Equation (6) from being amplified, the noise in $I_2$ can be reduced by forming a threshold. For example, a CSF mask can be generated in which only the pixels that have a signal portion in $I_2$ that is greater than the threshold are taken into account. The other pixels are set to 0 in $I_2$. Equation (6) can therefore be written as follows:

$$I_{non-csf} = \frac{c_{csf} I_1 + b I_2}{c_{csf}} \qquad (8)$$

wherein b is the binary CSF mask in order to discard pixels with low signal portion in $I_2$.

As is apparent from Equation (8), an image that takes into account an intensity of the other signal components can be calculated with the aid of the signal of the first signal acquisition, with the aid of the signal of the second signal acquisition and with the aid of the calculated scaling factor $c_{csf}$, wherein the signals of the cerebrospinal fluid are suppressed.

The present invention has the advantage that no inversion recovery technique is used, whereby the total acquisition time is reduced relative to conventional inversion recovery methods. Furthermore, a very good $T_2$ contrast is achieved in the image relative to images that were generated with a conventional inversion recovery method. An additional, important advantage is that the signal intensity of pathological tissues and multiple sclerosis is not suppressed since both the phase information and magnitude information is used. Furthermore, the background signal (for example of fat, blood, liver etc.) can be better suppressed, the radiated RF power is reduced and a $T_2$ weighting is achieved that is not sensitive to the magnetic field gradients that are used in imaging. The invention can always be applied when various tissue components which have different $T_1$ and $T_2$ times should be presented separate from one another. The different $T_1$ time is in particular necessary in order to achieve the opposite phase position after the time span $T_{Relax1}$.

Although modifications and changes may be suggested by those skilled in the art, it is the intention of the inventor to embody within the patent warranted hereon all changes and modifications as reasonably and properly come within the scope of his or her contribution to the art.

I claim as my invention:

1. A magnetic resonance imaging method to separate a signal component produced by cerebrospinal fluid, in a magnetic resonance signal, from other signal components in said magnetic resonance signal, comprising the steps of:

placing an examination subject, containing cerebrospinal fluid, in a magnetic resonance data acquisition unit and operating said magnetic resonance data acquisition unit to execute a first signal acquisition sequence to obtain a magnetic resonance signal from the examination subject in which all signal components, including a signal component produced by said cerebrospinal fluid, have the same phase position;

operating said magnetic resonance data acquisition unit with said examination subject therein to execute a second signal acquisition sequence with spin echo-based signals to require a magnetic resonance signal wherein the signal component produced by said cerebrospinal fluid has a phase position that is opposite to other signal components in said magnetic resonance signal obtained with said second signal acquisition sequence; and supplying said magnetic resonance signals obtained with said first signal acquisition sequence and said magnetic resonance signals obtained with said second signal acquisition sequence to an image processor and, in said image processor, automatically processing said magnetic resonance signals obtained with said first signal acquisition sequence together with said magnetic resonance signals obtained with said second signal acquisition sequence to produce a magnetic resonance image of the subject in which the signal component produced by said cerebrospinal fluid is substantially suppressed.

2. A method as claimed in claim 1 wherein said cerebrospinal fluid has a $T_1$ time constant, and comprising, after executing said first signal acquisition sequence, waiting, for a time span $T_{Relax1}$, that is smaller than said $T_1$ time constant of the cerebrospinal fluid, before executing said second signal acquisition sequence.

3. A method as claimed in claim 2 comprising repeating execution of said first and second signal acquisition sequences, and after executing said second signal acquisition sequence and before repeating execution of said first signal acquisition sequence, waiting for a time span $T_{Relax2}$ that is longer than $T_{Relax1}$.

4. A method as claimed in claim 3 wherein $T_{Relax2}$ is between 3 and 50 times longer than $T_{Relax1}$.

5. A method as claimed in claim 1 comprising, in said magnetic resonance data acquisition unit, generating a polarization field in which the examination subject is situated and, at an end of said first signal acquisition sequence, inverting magnetization in the examination subject counter to a direction of said polarization field.

6. A method as claimed in claim 1 comprising, in said first and second signal acquisition sequences, emitting refocusing pulses that produce multiple spin echo signals with respectively different flip angles in the respective magnetic resonance signals.

7. A method as claimed in claim 1 comprising, in said magnetic resonance data acquisition unit, generating a polarization field in which the examination subject is situated and, at an end of said first signal acquisition sequence, inverting magnetization in the examination subject counter to a direction of said polarization field by radiating an RF pulse series into the examination subject, comprising RF pulses that first maximize said magnetization in a transverse plane of the examination subject and subsequently inverting the maximized magnetization in said transverse plane.

8. A method as claimed in claim 7 wherein said cerebrospinal fluid has a $T_1$ time constant and comprising generating a polarization field in said magnetic resonance data acquisition unit in which the examination subject is located, and waiting, after executing said first signal acquisition sequence and before beginning said second signal acquisition sequence, for a time span $T_{Relax1}$ that is smaller than said $T_1$ time constant of the cerebrospinal fluid, and selecting $T_{Relax1}$ to cause, after expiration of $T_{Relax1}$, a magnetization component of the cerebrospinal fluid in said transverse plane is still aligned opposite a direction of the polarization field while respective magnetization components of some other signal components is aligned parallel to the direction of the polarization field.

9. A method as claimed in claim 1 comprising, in said image processor, automatically generating said magnetic resonance image in which said signal contribution of said cerebrospinal fluid is substantially suppressed using said magnetic resonance signal obtain by execution of said first signal acquisition sequence, said magnetic resonance signal obtained by execution of said second signal acquisition sequence, and a scaling factor that represents a signal ratio of magnetization of said cerebrospinal fluid to a total of said magnetic resonance signal obtained by execution of said second signal acquisition sequence.

10. A method as claimed in claim 9 comprising determining said scaling factor using the Bloch equations.

11. A method as claimed in claim 1 wherein said signal obtained by execution of said second signal acquisition sequence represents image pixels and, in said image processor when generating said magnetic resonance image in which said signal contribution of said cerebrospinal fluid is substantially suppressed, using only pixels, represented in said signal obtained by execution of said second signal acquisition sequence, that exceed a predetermined threshold.

12. A magnetic resonance system, comprising:

a magnetic resonance data acquisition unit adapted to receive an examination subject, containing cerebrospinal fluid therein;

a control unit configured to operate said magnetic resonance data acquisition unit to execute a first signal acquisition sequence to obtain a magnetic resonance signal from the examination subject in which all signal components, including a signal component produced by said cerebrospinal fluid, have the same phase position, operate said magnetic resonance data acquisition unit with said examination subject therein to execute a second signal acquisition sequence with spin echo-based signals to require a magnetic resonance signal wherein the signal component produced by said cerebrospinal fluid has a phase position that is opposite to other signal components in said magnetic resonance signal obtained with said second signal acquisition sequence; and an image processor supplied with said magnetic resonance signals obtained with said first signal acquisition sequence and said magnetic resonance signals obtained with said second signal acquisition sequence to said image processor being configured to automatically process said magnetic resonance signals obtained with said first signal acquisition sequence together with said magnetic resonance signals obtained with said second signal acquisition sequence to produce a magnetic resonance image of the subject in which the signal component produced by said cerebrospinal fluid is substantially suppressed.

* * * * *